(12) United States Patent
Chen et al.

(10) Patent No.: US 10,709,360 B2
(45) Date of Patent: Jul. 14, 2020

(54) MEDICAL DEVICE WITH INTEGRATED BIOSENSOR

(71) Applicant: BIOCREDE INC., Plymouth, MI (US)

(72) Inventors: Hao Chen, Ann Arbor, MI (US);
Alexander Wolf, Ann Arbor, MI (US);
Kevin Renehan, South Lyon, MI (US)

(73) Assignee: BIOCREDE INC., San Diego, CA (US)

( * ) Notice: Subject to any disclaimer, the term of this patent is extended or adjusted under 35 U.S.C. 154(b) by 135 days.

(21) Appl. No.: 16/121,405

(22) Filed: Sep. 4, 2018

(65) Prior Publication Data

US 2019/0069820 A1    Mar. 7, 2019

Related U.S. Application Data

(60) Provisional application No. 62/553,832, filed on Sep. 2, 2017.

(51) Int. Cl.
| | | |
|---|---|---|
| *A61B 5/145* | (2006.01) | |
| *A61B 5/00* | (2006.01) | |
| *A61B 5/1486* | (2006.01) | |
| *C12Q 1/00* | (2006.01) | |

(52) U.S. Cl.
CPC ...... *A61B 5/14503* (2013.01); *A61B 5/14532* (2013.01); *A61B 5/6852* (2013.01); *A61B 5/14546* (2013.01); *A61B 5/14865* (2013.01); *A61L 2300/114* (2013.01); *A61M 2202/0275* (2013.01); *C12Q 1/005* (2013.01)

(58) Field of Classification Search
None
See application file for complete search history.

(56) References Cited

U.S. PATENT DOCUMENTS

| 7,128,904 B2* | 10/2006 | Batchelor | A61K 33/34 424/94.4 |
|---|---|---|---|
| 2006/0008529 A1* | 1/2006 | Meyerhoff | A61K 31/21 424/486 |
| 2006/0039950 A1* | 2/2006 | Zhou | A61K 31/655 424/423 |
| 2006/0079740 A1 | 4/2006 | Silver et al. | |
| 2006/0106331 A1* | 5/2006 | Gorsuch | A61M 1/3672 604/6.09 |
| 2007/0106247 A1* | 5/2007 | Burnett | A61M 25/003 604/508 |
| 2008/0013960 A1* | 1/2008 | Tearney | A61B 5/0062 398/139 |
| 2008/0262330 A1 | 10/2008 | Reynolds et al. | |

(Continued)

*Primary Examiner* — Michael R Bloch
(74) *Attorney, Agent, or Firm* — Coastal Patent Law Group, P.C.

(57) ABSTRACT

The disclosure concerns medical devices configured to utilize nitric oxide (NO) donor materials to release NO gas upon contact with moisture in order to mitigate bacterial proliferation, coagulation, or a combination thereof, at a site of a biosensor integrated within the medical device. A novel multi-lumen medical device is described, the device having a first lumen for containing the NO donor material and producing the NO gas, and having a second lumen for housing biosensor componentry. A channel between the first and second lumens serves to communicate NO gas from the first lumen to a sensor-volume of the biosensor.

21 Claims, 4 Drawing Sheets

(56) References Cited

U.S. PATENT DOCUMENTS

| | | | |
|---|---|---|---|
| 2009/0069743 A1* | 3/2009 | Krishnamoorthy | A61B 5/1459 604/66 |
| 2010/0297200 A1 | 11/2010 | Schoenfisch et al. | |
| 2011/0024307 A1 | 2/2011 | Simpson et al. | |
| 2013/0261537 A1* | 10/2013 | Hofler | A61M 25/0043 604/23 |
| 2014/0294672 A1* | 10/2014 | Meyerhoff | A61M 1/342 422/48 |
| 2015/0073331 A1* | 3/2015 | Hofler | A61M 25/0043 604/23 |
| 2015/0366831 A1* | 12/2015 | Brisbois | A61L 29/16 424/484 |
| 2016/0339197 A1* | 11/2016 | Meyerhoff | A61M 35/00 |
| 2017/0028106 A1 | 2/2017 | Brisbois et al. | |

* cited by examiner

MEDICAL DEVICE WITH INTEGRATED BIOSENSOR

CROSS-REFERENCE TO RELATED APPLICATIONS

The application claims benefit of U.S. Provisional Application Ser. No. 62/553,832, filed 2 Sep. 2017; the entire contents of which are hereby incorporated by reference.

BACKGROUND

Field of the Invention

The invention relates to medical devices; and more particularly, to catheters and similar medical devices being configured with one or more integrated biosensors for detecting glucose, lactate, or any other analytes of interest, or combinations thereof.

Description of the Related Art

There are various diagnostic and therapeutic medical treatments that require the analysis of the concentrations of biological components found in the blood or subcutaneous fluids. Blood or fluid samples drawn from the patient which are subsequently analyzed by point-of-care devices offer very accurate concentration measurements but are often separated by long intervals, either due to restrictions placed on the frequency of draws and of the quantity of draws that can be made from the patient, or both, especially in the pediatric or neonatal intensive care units (PICU and NICU). Such point-of-care devices are expensive to maintain and can be hindered by limited sample throughput, especially in the intensive care unit which could have a large number of patients, all requiring frequent analyte monitoring. Insertion or contact of a low-profile medical device into the human body or onto the human tissue capable of accurate and continuous measurement is a viable alternative which is capable of providing accurate analyte readings at higher frequencies.

SUMMARY OF INVENTION

Conventional medical devices with integrated biosensors are susceptible to coagulation, biofilm formation, or both, at the sensor componentry, limiting the quality of sensing and useful duration for such biosensors.

Medical devices are disclosed which can be configured to utilize nitric oxide (NO) donor materials to release NO gas upon contact with moisture in order to mitigate bacterial proliferation, coagulation, or a combination thereof, at a site of a biosensor integrated within the medical device.

A novel multi-lumen medical device is described, the device having a first lumen for containing the NO donor material and producing the NO gas, and having a second lumen for housing biosensor componentry. A channel between the first and second lumens serves to communicate NO gas from the first lumen to a sensor-volume of the biosensor.

Unique compositions are described, and innovative structural features and inter-component relationships, such as the arrangement of various composition layers, are also described, which compositions, structures and relations serve to achieve the objectives as set forth herein, namely, providing a medical device with integrated biosensor(s) to measure analytes in human and animal patients, the biosensor(s) being adapted for mitigation of bacterial proliferation and/or coagulation using the communication of NO gas.

The described medical devices with integrated biosensors provide: (i) improved duration of use due to anti-bacterial and anti-coagulation effects of the NO gas; and (ii) improved sensing due to reduced interferences.

Other solutions to these and other problems are described herein.

BRIEF DESCRIPTION OF DRAWINGS

These and other features of the invention will become apparent to one having the ordinary level of skill in the art upon a thorough review of the following details and descriptions, particularly when reviewed in conjunction with the drawings, wherein.

DESCRIPTION OF EMBODIMENTS

Figure 1:
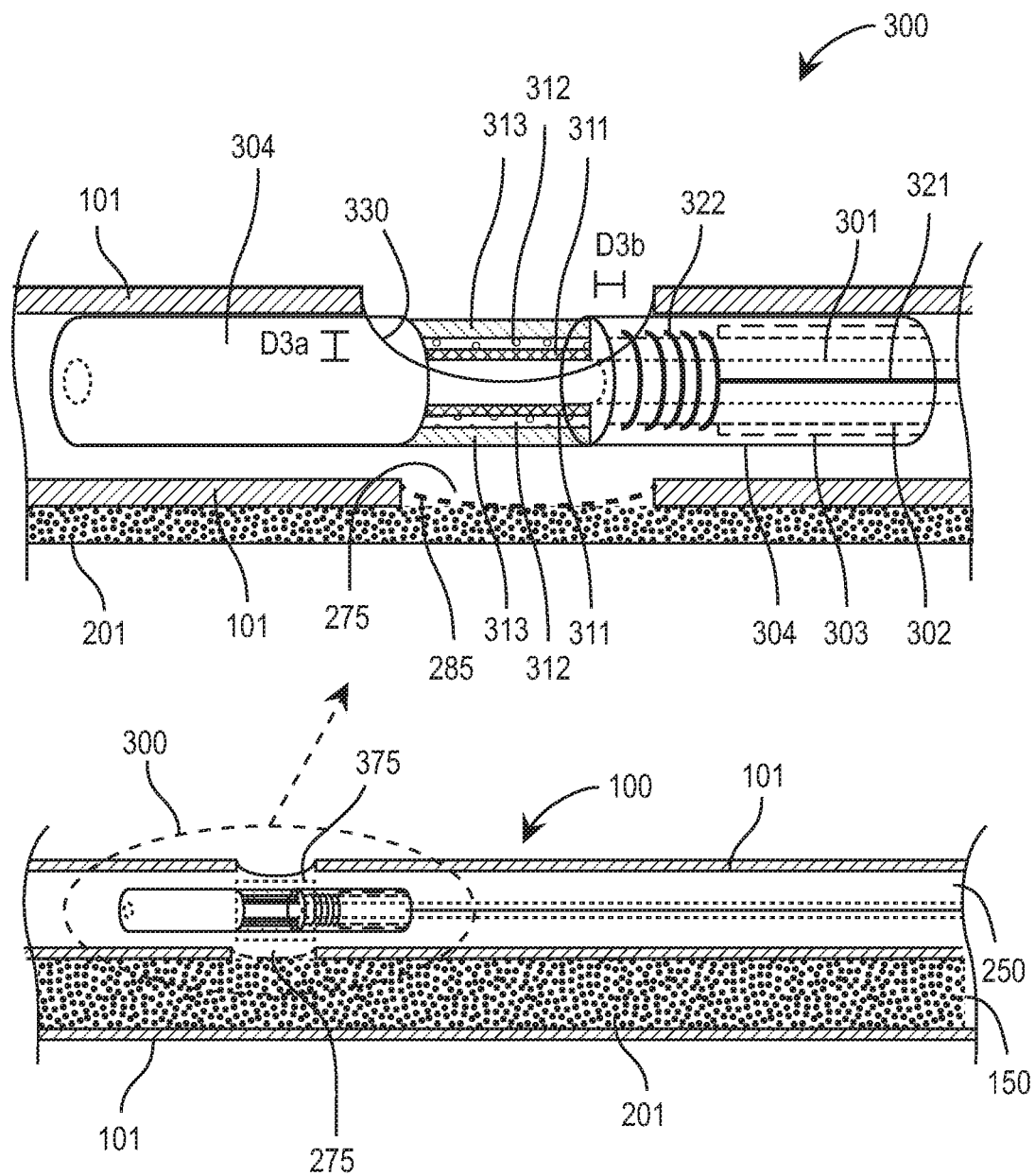
FIG. 1 shows a medical device with integrated biosensor in accordance with an embodiment.

For purposes of explanation and not limitation, details and descriptions of certain preferred embodiments are hereinafter provided such that one having ordinary skill in the art may be enabled to make and use the invention. These details and descriptions are representative only of certain preferred embodiments, however, and a myriad of other embodiments which will not be expressly described will be readily understood by one having skill in the art upon a thorough review of the instant disclosure. Accordingly, any reviewer of the instant disclosure should interpret the scope of the invention only by the claims, as such scope is not intended to be limited by the embodiments described and illustrated herein.

General Embodiment

In accordance with a general embodiment, a medical device with integrated bio-sensor is disclosed. The medical device comprises: a tubular body, the tubular body comprises a first lumen and a second lumen therein; the first lumen comprising a nitric oxide donor material disposed therein, wherein the nitric oxide donor material is configured to release nitric oxide gas upon contact with moisture; and the second lumen, being longitudinally disposed parallel with respect to the first lumen, is configured to house componentry of at least a first biosensor, the first biosensor having a first sensor-volume associated therewith; wherein a first nitric oxide channel is disposed between the nitric oxide donor material and the first sensor-volume, the first nitric oxide channel being configured to direct a flow of the nitric oxide gas into the first sensor-volume for preventing bacterial-proliferation, coagulation, or a combination thereof.

The first bio-sensor may comprise: a working electrode and a reference electrode. The working electrode generally includes: an insulation layer covering at least a portion of the working electrode and configured to restrict diffusion of electroactive interference compounds through the insulation layer; an analyte reaction layer comprising one or more immobilized or chemically linked antibodies, redox enzymes, or chelators for reacting with one or more corresponding analytes to achieve a detectable signal; and an analyte diffusion-control layer for regulating diffusion of analytes of interest into the first sensor-volume of the first biosensor. The reference electrode is generally positioned in proximity to the working electrode; however, the reference electrode is generally separated from the working electrode by a distance of between 0.2 um and 10.0 mm. In this regard, a terminal end of the reference electrode is generally spaced apart from a periphery of the aperture by a distance of up to 3.0 mm.

The medical device may optionally comprise a membrane disposed at a nitric oxide channel separating the first and second lumens. The membrane may comprise silicone.

The nitric oxide donor material is selected to be one that is configured to release nitric oxide gas in response to contact with moisture. Examples of such a nitric oxide donor material include, but are not limited to, diazeniumdiolated diamine, S-nitroso-albumin, S-nitroso-N-penicillamine (SNAP), S-nistrosocystine (CysNO), S-nitrosoglutathione (GSNO), diazeniumdiolated dibutylhexyldiamine (DBHD N2O2), Diethylenetriamine/nitric oxide adduct (DEAT/NO), Diethylamine NONOate (DEA/NO), Dipropylenetriamine NONOate (DPTA/NO), 6-(2-Hydroxy-1-methyl-2-nitrosohydrazino)-N-methyl-1-hexanamine (MAHMA/NO) or any combination thereof.

In certain embodiments, the nitric oxide donor material may comprise between 0.1% and 4.0% by weight SNAP, and up to 99.9% by weight excipient.

The term "excipient" is herein defined as "an inactive substance that serves as the vehicle or medium for an active substance." Examples of such excipients which are suitable for the disclosed invention include, but are not limited to, cellulose, crosspovidone, hydroxypropyl cellulose, hydroxylpropyl methyl cellulose, sorbitol, xylitol, povidone (PVP), perfluoroelastomer, perfluorosulfonic acid isomers, ethylene, vinyl fluoride, vinylidene fluoride, chlorotrifluoroethylene, propylene, hexafluoropropylene, perfluoropropylvinylether, perfluoromethylvinylether, silicone, polyethylene, polyurethane, or any combination thereof.

To make use of a detected signal, each of the working and reference electrodes are coupled to an electrode signal monitoring system for receiving and processing signals thereof.

In preferred embodiments, the working electrode comprises gold, platinum, silver, mercury, stainless steel, or carbon.

The reference electrode is generally positioned between 0.2 mm and 10.0 mm from the analyte reaction layer. In this regard, if placed too close the reference electrode may short circuit, whereas if placed too far away no signal is achieved.

In one unique aspect, the insulation layer of the medical device may comprise: one or more perflourinated sulfonic acid resin-containing sub-layers, and a plurality of electropolymerized sub-layers disposed on an outer surface of the perflourinated sulfonic acid resin-containing sub-layers. The term "perflourinated sulfonic acid resin (PFSA)" is a generic term used to describe NAFION® (available from Sigma Aldrich), and includes all variants thereof which would be appreciated by one with skill in the art. A thickness of the insulation layer may comprise between 0.1 um and 100.0 μm.

In various embodiments, the perflourinated sulfonic acid resin-containing sub-layers may comprise sulfonated tetrafluoroethylene and one or more of: perfluoro (alkyl vinyl ether), sulfonyl acid fluoride, perfluorocycloalkene, ethylene, vinyl fluoride, vinylidene fluoride, chlorotrifluoroethylene, propylene, hexafluoropropylene, perfluoropropylvinylether, perfluoromethylvinylether, polychlorotrifluoroethylene, perfluoroalkoxy polymer, fluorinated ethylene-propylene, polyethylenetetrafluoroethylene, polyethylenechlorotrifluoroethylene, perfluoroelastomer, tetrafluoroethylene-propylene, polyurethane, polyetheline, silicone, or any combination thereof.

Moreover, in preferred embodiments the perflourinated sulfonic acid resin-containing sub-layers comprise annealed sulfonated tetrafluoroethylene. In this regard, pores in the sulfonated tetrafluoroethylene are reduced in size, or eliminated altogether, when the perflourinated sulfonic acid resin-containing sub-layers are annealed.

In some embodiments, the electropolymerized sub-layers may comprise: 1,3 diaminobenzene, resorcinol, or a combination thereof. Generally, the medical device with integrated biosensor(s) is coated with the perflourinated sulfonic acid resin-containing sub-layers at a site where a portion of a working electrode is exposed at an aperture. The perflourinated sulfonic acid resin-containing sub-layers are annealed as described above. Next, the medical device with biosensor(s) is placed in a polymerization bath, where voltage and current are applied to cause electro-polymerization, in many layers above the perflourinated sulfonic acid resin-containing sub-layers.

In various embodiments, the analyte reaction layer can comprise enzymes selected from the group consisting of: creatinase, creatine amidohydrolase, sarcosine oxidase, malate oxidase, alcohol dehydrogenase, D-aspartate oxidase, spermine oxidase, NAD(P)H oxidase, urate oxidase, lactate oxidase, alcohol oxidase, pyruvate oxidase, glucose oxidase, glutamate oxidase, choline oxidase, glutathione sulfhydryl oxidase, cholesterol oxidase, histamine oxidase, L-lysine oxidase, L-aspartate oxidase, glycine oxidase, and galactose oxidase. The enzyme(s) of the analyte reaction are generally attached to an outer surface of the insulation layer using a bonding intermediate, such as but not limited to, glutaraldehyde or polymerized glutaraldehyde structures.

The analyte diffusion-control layer may comprise: 30-70% by weight polyurethane, 20-60% by weight silicone, and up to 50% of one or more of the following: poloxamer polyol surfactant, polylactic acid, polyglycolide, poly lactic-co-glycolic acid.

In some embodiments, one of: the insulation layer, the analyte reaction layer, and the diffusion-control layer, may further comprise a second nitric oxide donor material that is distinct from the first nitric oxide donor material.

In some embodiments, the reference electrode may comprise a coiled wire, the coiled wire being wound about at least a portion of a sleeve surrounding the working electrode for maximizing surface area thereof. In other embodiments, the reference electrode may comprise a conductive trace disposed on a sleeve, wherein the sleeve is disposed between the reference electrode and a wire component of the working electrode. In some embodiments, the reference electrode comprises a trace printed on a coating applied to the working electrode.

In some embodiments, the first bio-sensor may be configured to detect glucose. In other embodiments, the first bio-sensor may be configured to detect lactate. In some embodiments, the first sensor may be configured to detect glucose and the second bio-sensor is configured to detect lactate, or vice versa.

The medical device may include a second bio-sensor, the second bio-sensor being disposed a first distance from the first bio-sensor, wherein the first distance comprises between 5.0 mm and 50.0 mm.

In some embodiments, the medical device may comprise a third lumen, the third lumen being configured to receive one of: a guidewire or fluids. In other embodiments, the medical device may comprise a fourth lumen, the fourth lumen being configured to independently receive one of: a guidewire or fluids, or a nitric oxide donor material. The medical device may alternatively comprise four or more lumens.

The medical device of claim generally comprises at least one an aperture (330) extending through the tubular body of the medical device into a portion of the second lumen, wherein the aperture is disposed adjacent to the first sensor-volume of the biosensor. The aperture generally serves to expose the biosensor components to peripheral blood within the circulation of a patient for receiving detectable analyte. The medical device may comprise an outer layer covering the aperture and portions of the biosensor exposed therethrough, wherein the outer layer comprising silicone.

Illustrated Embodiments

Now turning to the drawings, in accordance with the illustrated embodiments, FIG. 1 shows a medical device with integrated biosensor in accordance with a first embodiment, wherein a tubular body of a medical device 100 is configured with a first lumen 150 and a second lumen 250. The first lumen comprises a nitric oxide (NO) donor material 201 disposed therein. The nitric oxide donor material is configured to provide NO gas upon contact with moisture. In this regard, when the device is placed in the body, moisture permeates the tubular body 101 into the first lumen, where it saturates the NO donor material, thereby releasing NO gas. The NO gas is communicated from the first lumen to a second lumen through a channel 275. The channel is positioned next to a sensor-volume 375 associated with a biosensor 300.

The biosensor generally comprises an insulation layer 311, an analyte reaction layer 312, and an analyte diffusion-control layer 313, collectively the "applied layers". The insulation layer is applied to a wire portion of the working electrode 301, where a section of about 1.0 mm of a PFA sleeve has been removed. As described elsewhere herein, the insulation layer comprises multiple sub-layers, including, a plurality of perflourinated sulfonic acid resin-containing sub-layers and a plurality of electropolymerized sub-layers. The analyte reaction layer is applied on an outer surface of the insulation layer. Finally, the analyte diffusion-control layer is applied on an outer surface of the analyte reaction layer.

The working electrode wire is generally covered in a TEFLON® coating (or "perfluoroalkoxy copolymer resin (PFA)"), or any similar material, except where removed at the site of the applied layers. Above the PFA coating 302, and adjacent to the sensor volume, is applied a reference electrode 321, which is illustrated as being coupled to a coiled wire 322 at a terminal end thereof, though the coiled wire may alternatively be substituted with a printed or applied trace on an outer surface of the PFA coating. Heat-shrink tubing 303 is applied to the portions of the electrode which do not require exposure, and heat is applied. In this regard, the wires and electrodes are secure and immobilized. A polyurethane top coat 304 is applied to the assembly, including the heat-shrink tubing and biosensor components within the sensor-volume.

The working electrode, insulation layer, analyte reaction layer, and an analyte diffusion-control layer, coupled with the reference electrode, collectively define the functional biosensor 300.

The biosensor is placed in the second lumen 250, at a location adjacent to an aperture 330 of the tubular body 101. Generally, the tubular body is modified by a laser for etching the aperture and channel, respectively, though other techniques may be similarly implemented. Prior to introducing the biosensor, an optional silicone coating may be applied to the channel to form a membrane 285 between the second lumen and the NO donor material. The silicone membrane will be permeable to moisture and NO gas.

For purposes of clarity, a relevant portion of the biosensor is shown in zoomed portion of FIG. 1.

A third distance is represented in FIG. 1 and relates to the distance between the reference electrode and the working electrode. The reference electrode must be close enough to the working electrode to obtain a signal, but not too close to short circuit. A radial component (D3a) of the distance between the reference and working electrodes (generally, thickness of the PTFE coating on the working electrode wire) comprises between about 0.2 mm and 5.0 mm. A longitudinal component (D3b) of the distance between the working and reference electrodes, functionally defining a gap between the analyte reaction layer and the reference electrode, comprises between about 0.2 mm and 10.0 mm. Accordingly, it can be said that the distance between the working and reference electrodes, or third distance, comprises between 0.2 mm and 10.0 mm. It is preferred that the reference electrode, if including a coiled wire, should comprise at least ten windings, such that the surface area of the coils is at least twice the surface area of the working electrode. In any embodiment, the surface area of the reference electrode should be about two times the surface area of the working electrode.

Figure 2:
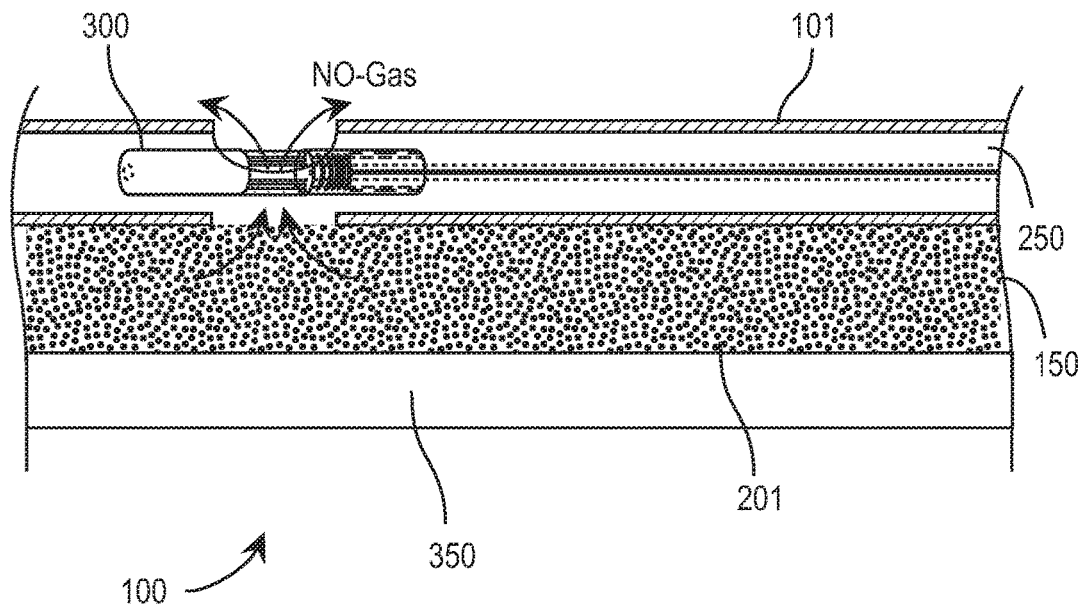
FIG. 2 further illustrates the medical device with integrated biosensor of FIG. 1 which is configured to produce nitric oxide gas upon contact with moisture, and to communicate the nitric oxide gas through a channel and toward a sensor-volume associated with the bio sensor.

FIG. 2 further illustrates a medical device 100 with integrated biosensor 300 which is configured to produce nitric oxide gas ("NO-Gas") upon contact of the NO donor material 201 with moisture, and to communicate the nitric oxide gas through the channel and around sensor-volume associated with the biosensor. As shown, the nitric oxide donor material is contained in first lumen 150, whereas the biosensor componentry is contained in second lumen 250. A third lumen 350 is further shown, wherein the third lumen can be used for translating a guidewire, communicating drug or fluids to the patient, or a combination thereof.

The tubular body 101 may be manufactured by extrusion to contain any desired number of lumens. Looking at a cross section of the tubular body 101, the inner walls 199 become visible.

Figure 3A:
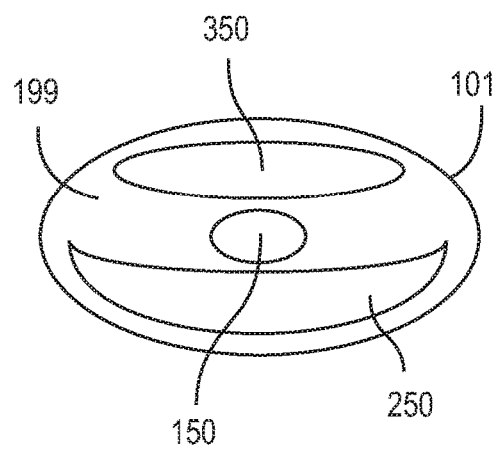
FIG. 3A shows a cross section of a tubular body of the medical device in accordance with another embodiment, the tubular body including three lumens.

FIG. 3A shows a cross section of a tubular body of the medical device in accordance with a three-lumen embodiment, the tubular body including a first lumen 150 disposed at a center of the tubular body; a second lumen 250 disposed at a periphery of the tubular body and a third lumen 350 disposed at the periphery of the tubular body and at a side opposite the second lumen. Other configurations may be similarly practiced.

Figure 3B:
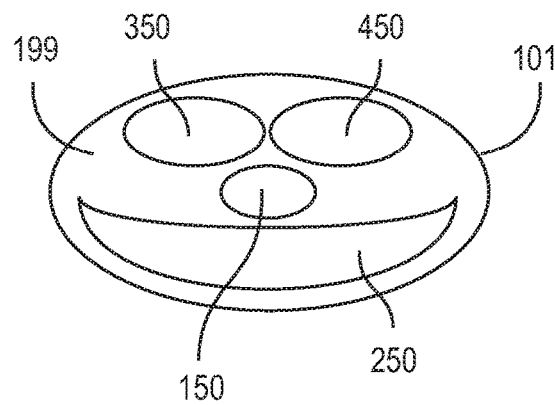
FIG. 3B shows a cross section of a tubular body of the medical device in accordance with yet another embodiment, the tubular body including four lumens.

FIG. 3B shows a cross section of a tubular body of the medical device in accordance with a four-lumen embodiment, the tubular body including first lumen 150, second lumen 250, third lumen 350, and fourth lumen 450. Also shown is the inner-wall 199 disposed between the lumens.

Figure 4:
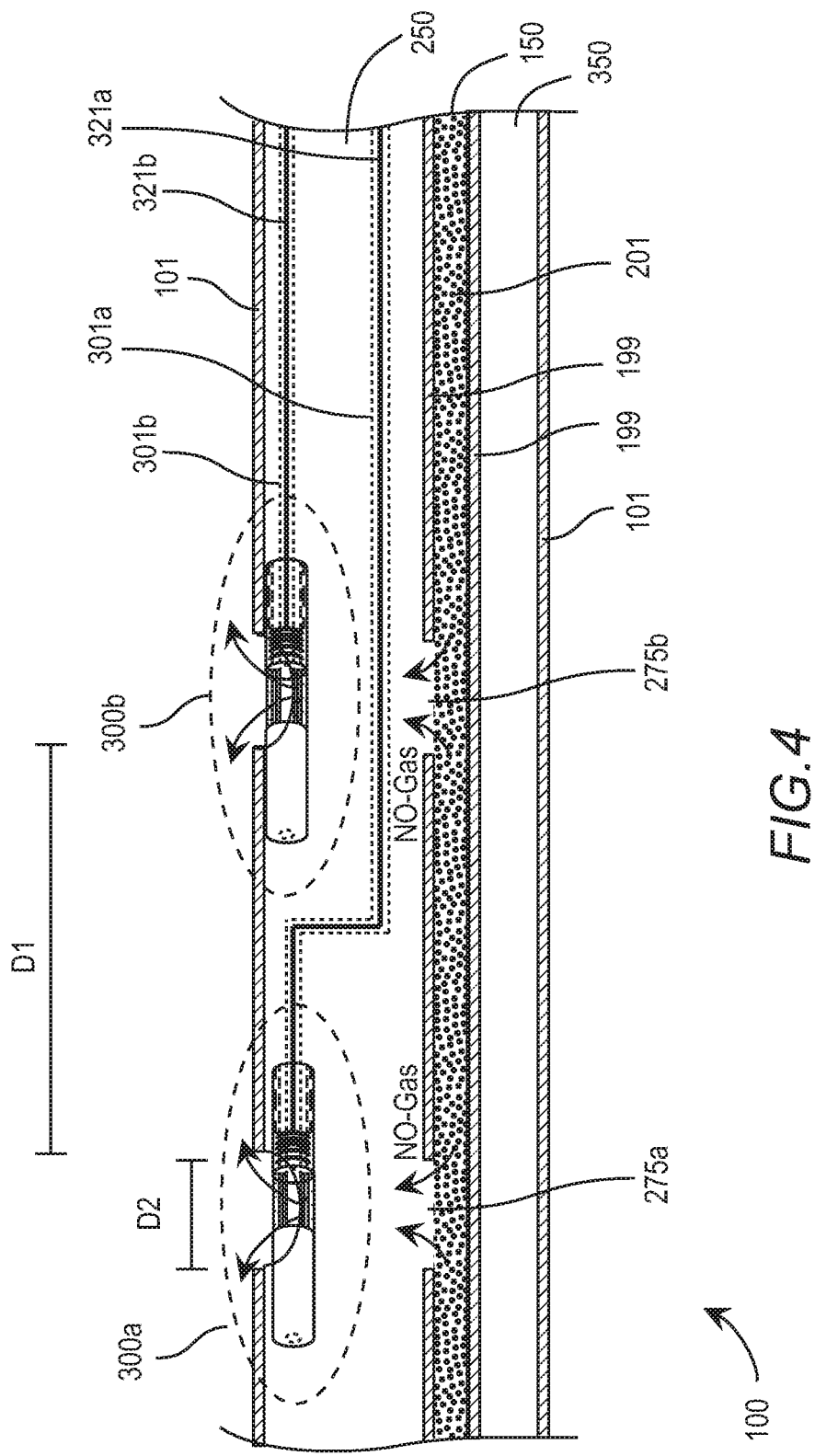
FIG. 4 shows a medical device with integrated biosensor in accordance with another embodiment.

FIG. 4 shows a medical device 100 with two integrated biosensors 300a; 300b, respectively, in accordance with another embodiment. Although two biosensors are shown, any plurality of biosensors may be implemented to the extend such biosensors can be fit within the lumen-space. The medical device comprises tubular body 101, and inner-walls 199. Between the tubular body periphery and the inner walls are at least three lumens (150; 250; 350, respectively). In first lumen 150 is disposed the nitric oxide donor material 201. A first biosensor 300a is shown having a first working electrode 301a, and a first reference electrode 321a each extending within the second lumen 250. A second biosensor 300b is shown having a second working electrode 301b, and a second reference electrode 321b each also extending within the second lumen 250. In this regard, the two biosensors are housed in the second lumen, which is oriented parallel to the first lumen and disposed adjacent thereto. Between the first biosensor 300a and the second lumen is a first NO channel 275a configured to communicate NO-Gas to a first sensor-volume of the first biosensor. Also, between the second biosensor 200b and the second lumen is a second NO channel 275b configured to communicate NO-Gas to a second sensor volume of the second biosensor. The second biosensor is positioned a distance D1 from the first biosensor, that is, between 5.0 mm and 50.0 mm, preferably between 10.0 mm and 20.0 mm. The aperture has a diameter (D2) between 0.1 mm and 10.0 mm, preferably 1.0 mm.

Figure 5:
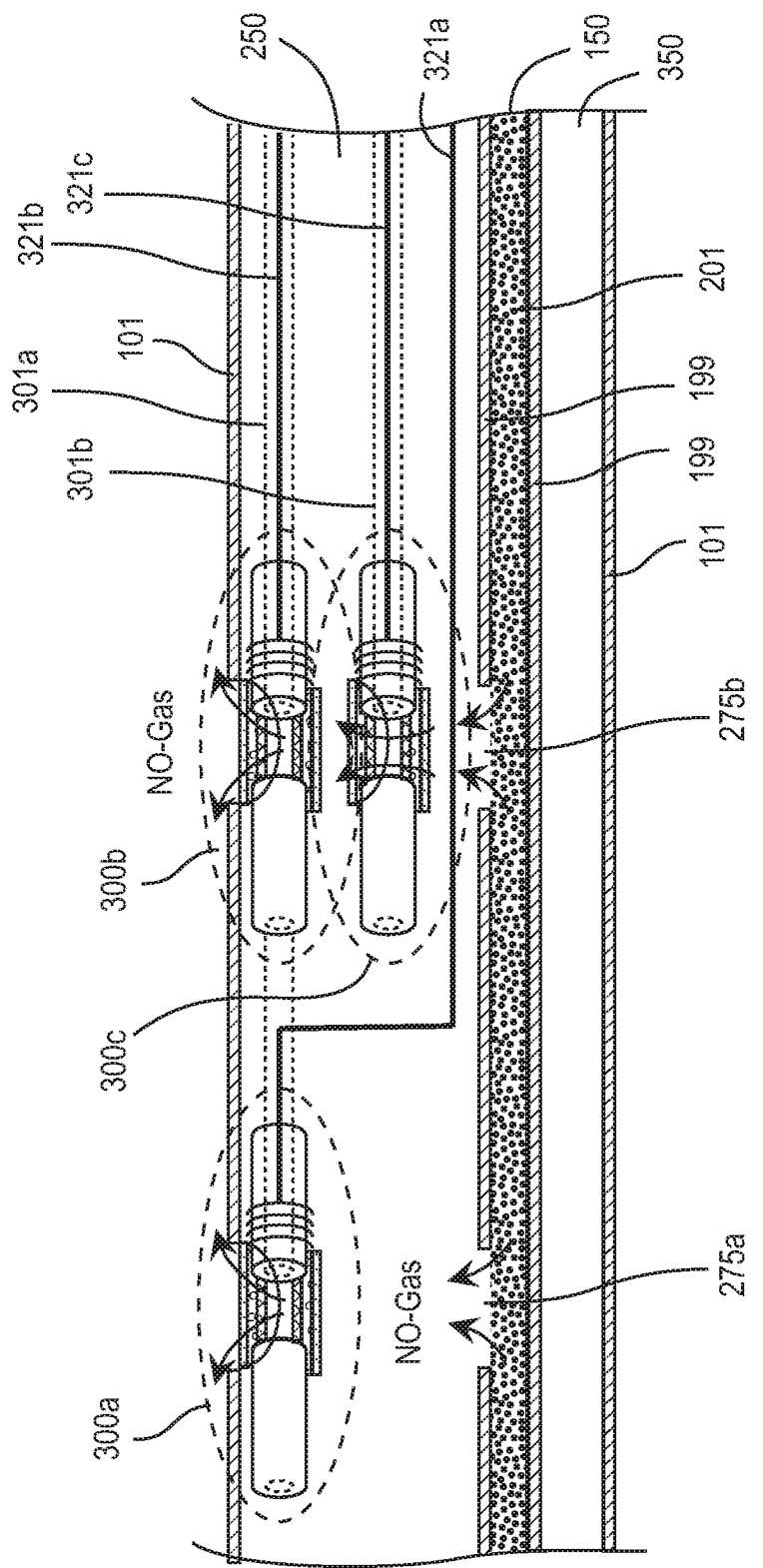
FIG. 5 shows a medical device with integrated biosensor in accordance with yet another embodiment.

FIG. 5 shows a medical device 100 with three integrated biosensors (300a; 300b; 300c, respectively) in accordance with yet another embodiment. Here, first and second biosensors share a common working electrode wire, whereas a third and independent biosensor is positioned adjacent to the second biosensor. The first biosensor is configured to detect a first analyte, and each of the second and third biosensors are configured to detect a second analyte, meaning that appropriate "applied layers" are applied to the corresponding electrodes. The value of the signal from the third biosensor 300c is used to measure the second analyte; whereas the value of the signal of the third bio sensor 300c is subtracted from the combined value of the first and second biosensors 300a; 300b to find a delta signal for measuring the first analyte.

The medical device comprises tubular body 101, and inner-walls 199. Between the tubular body periphery and the inner walls are at least three lumens (150; 250; 350, respectively). In first lumen 150 is disposed the nitric oxide donor material 201. A first biosensor 300a is shown having a first working electrode 301a, and a first reference electrode 321a each extending within the second lumen 250. A second biosensor 300b is shown sharing the first working electrode 301a, and further comprises a second reference electrode 321b each also extending within the second lumen 250. A third biosensor 300c comprises a second working electrode 301b and a third reference electrode 321c. In this regard, the three biosensors are each housed in the second lumen, which is oriented parallel to the first lumen and disposed adjacent thereto. Between the first biosensor 300a and the second lumen is a first NO channel 275a configured to communicate NO-Gas to a first sensor-volume of the first biosensor. Also, between the second and third biosensors 300b; 300c and the second lumen is a second NO channel 275b configured to communicate NO-Gas to a second sensor volume of the second biosensor and third sensor-volume of the third biosensor.

Each of the above embodiments illustrate a medical device with integrated biosensor(s) configured for improved function due to NO-Gas releasing components, such as a NO donor material and a channel within the inner-walls of the tubular body for communicating the NO-Gas.

The medical device with integrated biosensor as-described and claimed herein is applicable to human and animal medical clinics and hospitals for medical treatment. Specifically, the medical devices described herein are useful to detect analytes, such as but not limited to glucose and lactate in the blood of a patient, as well as for conventional uses of catheters and the like.

EXAMPLE 1: MANUFACTURE OF A MEDICAL DEVICE WITH INTEGRATED BIOSENSOR

Summary:

Nitric oxide (NO) releasing lactate and glucose amperometric electrochemical sensors (two electrode systems: working/reference) are manufactured after a series of steps, generally including: (i) cleaning the recipient working electrode leads; (ii) placing/polymerizing the insulation layers (including sub-layers); (iii) depositing and crosslinking analyte reaction layers; (iv) placing the analyte diffusion-control layers; (v) optionally mounting the sensors within a lumen of a medical device, such as a catheter, and more particularly a multi-lumen catheter; (vi) testing the sensors with a potentiostat device for evaluating analytical accuracy, or in a nitric oxide analyzer (NOA) for evaluating NO release magnitude, longevity, or both.

Materials:

Platinum-iridium wire (or similar working electrode wire), serves as a structural base for the biosensor as well as the working electrode, for which about 10% iridium content will be sufficient, whereas pure platinum wire would be too soft on its own. The PFA coating on the wire insulates the wire in all places except were it is removed by design, to prevent shorting during measurement.

Silver wire (or similar reference electrode wire), serves as the reference electrode once the exposed lead is coated in silver chloride (AgCl) for functionality in aqueous environments (PBS, containing Cl—). The PFA coating on the wire insulates the wire in all places except where it is removed by design, to prevent shorting of the sensor during measurement.

A perflourinated sulfonic acid resin (PFSA), such as commercially available NAFION® perflourinated resin solution (5 wt. % in lower aliphatic alcohols), is used for one of two insulation sub-layers. The PFSA can be heat treated (annealed) above its glass transition point (20-140° C.), typically 160-168° C. This annealed PFSA sub-layer blocks exchange of negatively charged ions, namely, ascorbate and urate, which generate interference current response through oxidation.

An electropolymerized film comprising 1-3 diaminobenzene (m-phenylenediamine) and resorcinol forms the second of two insulation sub-layers of the insulation layer of the biosensor. As a size-exclusion limiting layer, it selects against high molecular weight species, namely acetaminophen, which can generate interference current response through oxidation.

The functionality of the sensor is dependent upon the crosslinking/immobilization of enzymes, such as glucose oxidase and lactate oxidase, among others mentioned herein, which consume the analyte of interest (localized, no effect on bulk concentration) and produce hydrogen peroxide, which is subsequently oxidized at the working electrode interface to produce the response current signal proportional to the analyte concentration in the bulk solution.

The addition of outer layers to the sensors restricts the diffusion of the analyte of interest to the enzyme, making the enzyme co-factor oxygen the limiting reagent. This layer can be composed of a single polymer, such as, for example, E2As Elast-eon Polyurethane (2-5% solution), FG RTV silicone rubber (moisture curing), or PLURONIC F-127®, or a mixture of multiple polyurethanes in the solvent tetrahydrofuran (THF), anhydrous, inhibitor-free.

Without an analyte diffusion-control layer, the biosensor response may not have an operational linear range and can become a very sensitive, but binary analyte detector.

The sensor housing is typically a small multi-lumen catheter in which one lumen is devoted to housing the biosensor componentry. Apertures can be cut into the catheter/housing such that the biosensor has contact with the external solution. These apertures have been reproducibly created with a $CO_2$ laser etching machine.

The PFA coating of the two wire electrodes of the biosensor (working and reference) opposite of the solution-contacting ends must be stripped slightly so as to provide electrical contact interface with a potentiostat device. This is to supply the sensor with external voltage and measure the resulting current signal.

If a catheter housing is being implemented, these two electrode leads are often connected to the wireless, mobile potentiostat through a headphone jack connector. The long electrode leads are fed distal-to-proximal end (to avoid damaging the enzyme end) and soldered to the headphone jack.

UV-curing RTV may be used to secure the sensors once they have been placed, otherwise the biosensor may move away from the aperture and become inoperative.

A mixture of SNAP (RSNO) and UV-cure RTV has been used to fill the other catheter lumen with a NO release polymer, though other NO-releasing materials can be similarly implemented. A SNAP and RTV mixture can be stored in a syringe, chilled via refrigerator and used with a drill press to apply external pressure sufficient to fill the lumen, due to high solution viscosity.

Assembly Steps:

Day 1:

The working and reference electrodes are cut from the source spool of wire to a desired length and straightened to a desired degree. The wire is coated with PFA.

A small approximately 1 mm cavity is cut on the end of the working electrode. This can be accomplished with a razor blade and applying the "circle cut" technique. It is important to cut the PFA coating, but not cut deep enough to slice or cut the wire. Also, cut approximately 5 mm of PFA off the opposite end as a lead for connecting the electropolymerization wires.

Use latex gloved fingers with thumb and index fingernails to pull the PFA coating to create the working electrode area (exposed Pt/Ir wire), it is critical that this has a smaller surface area than the reference electrode. Cut off any excess PFA with the razor blade.

Clean the working electrodes by sonicating them in HCl, and then in ethanol.

Hang the wires vertically with the tips at the lower end. Use a wire loop (or small vial) to apply about five dip coating of perflourinated sulfonic acid resin (PFSA), drying between each application.

Prepare oven to about 165° C. for annealing the PFSA sub-layers.

After sufficient drying time, place the wires in the oven for annealing. Use glass to support the wires. Be careful not to disturb cavity/working electrode area.

Leave sensors at 165° C. for about an hour, then, turn the dial on the oven to the minimum/off.

Do not open oven door until the sensors and oven have reached room temperature. Rapid cooling causes the PFSA to crack or become ineffective.

While the oven is cooling, prepare an amount of PBS solution for electropolymerization and place under nitrogen ($N_2$) gas purge (needle) for prior to use in order to remove dissolved oxygen.

Add a first amount of the N2-purged PBS to one amber vial containing 1,3-diaminobenzene, add a second amount of the N2-purged PBS to another amber vial containing resorcinol, then combine these in a reaction cell.

Connect all working electrode leads to one working electrode cable from the potentiostat. All apertures should be in solution. Connect the reference electrode cable from the potentiostat to an Ag/AgCl electrode. The Ag/AgCl electrode can be commercial or a thick silver wire soaked in HCl/FeCl3 solution. The surface area of this Ag/AgCl electrode must be greater than the surface area of the combined Pt/Ir surface areas.

Perform cyclic voltammetry overnight, or for at least 6 hours.

Day 2:

Prepare enzyme solution(s) and glutaraldehyde solution(s) before the conclusion of electropolymerization.

Prepare Glucose Oxidase ("GOx") by combining bovine serum albumin (BSA), GOx enzyme, and deionized water, then mix thoroughly.

Prepare Gluteraldehyde-GOx (for GOx) by combining-glutaraldehyde and deionized water or phosphate buffered saline (PBS).

Prepare Lactate Oxidase by combining BSA, PBS, and polyethyleneimine (PEI), the combination forming "Solution 1". Combine Solution 1 with lactate oxidase enzyme.

Prepare Gluteraldehyde-LOx by combining glutaraldehyde, and PBS; note that a lower glutaraldehyde concentration is provided for LOx.

Remove potentiostat electrode wires, rinse the electrodes briefly with deionized water, and dry with a short burst of compressed air.

Secure the electrodes to place the enzyme solution into the aperture/working electrode area. Dissolve enzyme solution and make sure no enzyme residual remains in the vial.

Clean and prepare a gas-tight syringe by rinsing with deionized water.

Draw up the desired amount of enzyme for the number of sensors being prepared using about 0.5-1.0 uL for each sensor. Deposit the enzyme solution carefully, ensuring that the drop spans the gap between sections of PGA coating and coats the entire working electrode area. Thoroughly rinse the syringe after depositing all enzyme of the same type.

Let the enzyme solution drop dry on the sensor working area, for example about one hour depending on the enzyme.

Add glutaraldehyde solution to the working electrode area on top of the dried enzyme with the syringe. The glutaraldehyde should re-hydrate the enzyme. Make sure the entire area is coated with the glutaraldehyde and rinse the syringe.

Allow the enzyme-glutaraldehyde crosslinking to occur. The amount of time required for crosslinking is dependent on the enzyme involved, but may require one or two hours. Excessive crosslinking times, for example, longer than 12 hours, have been demonstrated to be detrimental to the enzyme function.

While enzyme/glutaraldehyde crosslinking is ongoing, prepare the reference electrodes for use on Day 3.

Cut lengths of PFA-coated Ag wire about 5 cm longer than the Pt/Ir working electrodes. Use a razor blade (or laser cutter) with circle cut technique to remove the PFA coating from one end of the wire, leaving an exposed reverence electrode area. Place these wires into the acidified HCL/FeCl3 solution for about one hour to generate the AgCl coating needed for reference electrode operation.

Prepare an analyte diffusion-control layer coating solution during enzyme/glutaraldehyde crosslinking. Measure out dry components including polyurethane, silicone RTV, PLURONIC F-127® (non-ionic surfactant polyol), and optionally a NO donor (SNAP, etc.). Add anhydrous tetrahydrofuran (THF) as a solvent portion of the outer layers in a glass container. Ensure a tight seal of the cap on the vial to minimize evaporation of the THF. Place a magnetic stir bar in the solution. Alternate placement between the 32° C. isotemp oven and on a stir plate. Leave solution overnight to mixt/stir, as some components may not dissolve initially.

Day 3:

Rinse the working electrodes (now with immobilized enzyme) in a vial of deionized water or PBS. This rinsing will dissolve and rinse away non-crosslinked enzyme.

Wrap the Ag/AgCl reference electrodes in a tight coil around the Pt/Ir/enzyme working electrodes. Ensure that the coil is in close proximity (within 1 cm of the enzyme area of the sensor), but is not situated on top of the enzyme.

Secure the Ag/AgCl electrode with polyethylene terephthalate (PET) heat shrink tubing placed over the working (Pt/Ir) and reference (Ag/Cl) electrode leads. These should be in close proximity to the coiled AgCl and enzyme areas so as to secure them together by not cover them. This heat shrink tubing also adds some structural reinforcement to the sensor assembly.

Use a heat gun or adjustable temperature hair dryer to activate and lock the heat-shrink tubing and the electrodes all in place. Electrodes that are not secured could come apart or become damaged.

Suspend the electrodes in order to apply the outer layers (analyte diffusion-control layer) through wire-loop casting or dip-coating.

Wire Loop Casting: deposit analyte diffusion-control layer coating solution onto the wire loop and pass it over the outer surface of the sensor assembly (usually about 2 cm) in an up and down pattern. For consistency between individual sensors, the loop should be rinsed with a dip in the THF solution and subsequently dried between applications of outer layer coating to each sensor. Allow each sensor to dry between coatings. About five to eight outer layer coatings should be applied to each sensor.

Dip Coating: partition an amount of the analyte diffusion-control layer coating solution to a thin vial, preferably with a sealable top to minimize THF evaporation. Dip each sensor into the small vial such that the same length (about 2 cm) is coated on each sensor to reinforce consistency between individual sensors. Allow each sensor to dry between coatings. Five to eight outer layer coatings should be applied to each sensor.

If the sensors will be put to immediate use, place them in PBS solution prior to connecting to a potentiostat. If, however, the sensors will be kept for storage and subsequent use, place in refrigerator or room temperature storage container. Freezing is not advised due to formation of micro fissures which can render the sensors inoperable.

The aforementioned steps are illustrative of one specific embodiment for practicing the invention; however, one having skill in the art will appreciate a myriad of possible alternative combinations and arrangements of the features disclosed herein. As such, the descriptions are intended to be enabling only, and non-limiting. Instead, the spirit and scope of the invention is set forth in the appended claims.

REFERENCE SIGNS LIST

Medical device (100)
Tubular body (101)
First lumen (150)
Inner-walls (199)
Nitric oxide donor material (201)
Second lumen (250)
Nitric oxide channel (275; 275a; 275b)
NO & $H_2O$ permeable membrane (285)
Biosensor (300; 300a; 300b)
Working electrode (301; 301a; 301b)
Polytetrafluoroethylene-based coating (302)
Heat-shrink tubing (303)
Polyurethane coating (304)
Insulation layer (311)
Analyte reaction layer (312)
Analyte diffusion-control layer (313)
Reference electrode (321; 321a; 321b; 321c)
Coiled wire (322)
Aperture (330)
Third lumen (350)
Sensor volume (375)
Fourth lumen (450)
First distance (D1)
Second distance (D2)
Third distance (D3a; D3b)

What is claimed is:

1. A medical device (100) with integrated bio-sensor, comprising:
   a tubular body (101), the tubular body comprising a first lumen (250) and a second lumen (350) therein;
   the first lumen comprising a nitric oxide donor material (201) disposed therein, wherein said nitric oxide donor material is configured to release nitric oxide gas;
   the second lumen being longitudinally disposed parallel with respect to the first lumen and configured to house componentry of at least a first biosensor (300), the first biosensor having a first sensor-volume (375) associated therewith;
   wherein a first nitric oxide channel (275) is disposed between the nitric oxide donor material and the first sensor-volume, the first nitric oxide channel being configured to direct a flow of the nitric oxide gas into the first sensor-volume for preventing bacterial-proliferation, coagulation, or a combination thereof,
   wherein the first biosensor and the nitric oxide donor material are each disposed in a distinct lumen of the first and second lumens.

2. The medical device of claim 1, wherein the first bio-sensor comprises:
   a working electrode (301) and a reference electrode (321), the working electrode comprising:
      an insulation layer (311) covering at least a portion of the working electrode and configured to restrict diffusion of electroactive interference compounds through the insulation layer;
      an analyte reaction layer (312) comprising one or more immobilized or chemically linked antibodies, redox enzymes, or chelators for reacting with one or more corresponding analytes to achieve a detectable signal; and an analyte diffusion-control layer (313) for regulating diffusion of analytes of interest into the first sensor-volume of the first biosensor;

the reference electrode being positioned in proximity to the working electrode.

3. The medical device of claim 2, wherein each of the working and reference electrodes are coupled to an electrode signal monitoring system.

4. The medical device of claim 2, wherein the insulation layer comprises: one or more perflourinated sulfonic acid resin-containing sub-layers, and a plurality of electropolymerized sub-layers disposed on an outer surface of the one or more perflourinated sulfonic acid resin-containing sub-layers.

5. The medical device of claim 4, wherein the one or more perflourinated sulfonic acid resin-containing sub-layers comprise sulfonated tetrafluoroethylene and one or more of: perfluoro (alkyl vinyl ether), sulfonyl acid fluoride, perfluorocycloalkene, vinyl fluoride, vinylidene fluoride, chlorotrifluoroethylene, propylene, hexafluoropropylene, perfluoropropylvinylether, perfluoromethylvinylether, polychlorotrifluoroethylene, perfluoroalkoxy polymer, fluorinated ethylene-propylene, polyethylenetetrafluoroethylene, polyethylenechlorotrifluoroethylene, perfluoroelastomer, tetrafluoroethylene-propylene, polyurethane, polyetheline, silicone or any combination thereof.

6. The medical device of claim 4, wherein the one or more perflourinated sulfonic acid resin-containing sub-layers comprise annealed perflourinated sulfonic acid resin.

7. The medical device of claim 2, wherein the reference electrode comprises:

a coiled wire, the coiled wire being wound about at least a portion of a sleeve surrounding the working electrode for maximizing surface area thereof, or a conductive trace disposed on the sleeve, wherein the sleeve is disposed between the reference electrode and a wire component of the working electrode.

8. The medical device of claim 2, wherein a thickness of the insulation layer comprises between 0.1 μm and 100.0 μm.

9. The medical device of claim 2, wherein the reference electrode is positioned between 0.2 mm and 10.0 mm from the analyte reaction layer.

10. The medical device of claim 2, wherein the one or more redox enzymes include: creatinase, creatine amidohydrolase, sarcosine oxidase, malate oxidase, alcohol dehydrogenase, D-aspartate oxidase, spermine oxidase, NAD(P)H oxidase, urate oxidase, lactate oxidase, alcohol oxidase, pyruvate oxidase, glucose oxidase, glutamate oxidase, choline oxidase, glutathione sulfhydryl oxidase, cholesterol oxidase, histamine oxidase, L-lysine oxidase, L-aspartate oxidase, glycine oxidase, or galactose oxidase.

11. The medical device of claim 2, wherein the analyte diffusion-control layer comprises: 30-70% by weight polyurethane, 20-60% by weight silicone, and up to 50% of one or more of the following: poloxamer polyol surfactant, polylactic acid, polyglycolide, poly lactic-co-glycolic acid.

12. The medical device of claim 2, wherein at least one of: the insulation layer, the analyte reaction layer, and the analyte diffusion-control layer, comprises a second nitric oxide donor material.

13. The medical device of claim 1, wherein the nitric oxide donor material is one that is configured to release nitric oxide gas in response to contact with moisture.

14. The medical device of claim 1, wherein said nitric oxide donor material comprises: diazeniumdiolated diamine, S-nitroso-albumin, S-nitroso-N-penicillamine (SNAP), S-nistrosocystine (CysNO), S-nitrosoglutathione (GSNO), diazeniumdiolated dibutylhexyldiamine (DBHD N202), Diethylenetriamine/nitric oxide adduct (DEAT/NO), Diethylamine NONOate (DEA/NO), Dipropylenetriamine NONOate (DPTA/NO), 6-(2-Hydroxy-1-methyl-2-nitrosohydrazino)-N-methyl-1-hexanamine (MAHMA/NO) or a combination thereof.

15. The medical device of claim 1, wherein said nitric oxide donor material comprises: between 0.1% and 4.0% by weight SNAP, and up to 99.9% by weight excipient.

16. The medical device of claim 15, wherein the excipient comprises: cellulose, crosspovidone, hydroxypropyl cellulose, hydroxylpropyl methyl cellulose, sorbitol, xylitol, povidone (PVP), perfluoroelastomer, perfluorosulfonic acid isomers, ethylene, vinyl fluoride, vinylidene fluoride, chlorotrifluoroethylene, propylene, hexafluoropropylene, perfluoropropylvinylether, perfluoromethylvinylether, silicone, polyethylene, polyurethane, or any combination thereof.

17. The medical device of claim 1, further comprising a second bio-sensor, the second bio-sensor being disposed a first distance (D1) from the first bio-sensor, wherein the first distance comprises between 5.0 mm and 50.0 mm.

18. The medical device of claim 1, further comprising a third lumen, the third lumen being configured to receive one of: a guidewire or fluid.

19. The medical device of claim 1, further comprising an aperture (330) extending through the tubular body into a portion of the second lumen, wherein the aperture is disposed adjacent to the first sensor-volume.

20. The medical device of claim 19, wherein the medical device comprises an outer layer covering the aperture and portions of the first biosensor exposed therethrough, the outer layer comprising silicone.

21. The medical device of claim 1, further comprising a membrane (285) disposed at the channel separating the first and second lumens; wherein the membrane comprises silicone.

* * * * *